(12) United States Patent
Farrell

(10) Patent No.: US 11,865,269 B2
(45) Date of Patent: Jan. 9, 2024

(54) HYDROPHILIC MEDICAL DEVICE WITH REMOVABLE MOISTURE CONTROL/BARRIER LAYER

(71) Applicant: Hollister Incorporated, Libertyville, IL (US)

(72) Inventor: David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 552 days.

(21) Appl. No.: 16/646,063

(22) PCT Filed: Sep. 10, 2018

(86) PCT No.: PCT/US2018/050263
§ 371 (c)(1),
(2) Date: Mar. 10, 2020

(87) PCT Pub. No.: WO2019/051412
PCT Pub. Date: Mar. 14, 2019

(65) Prior Publication Data
US 2020/0282177 A1 Sep. 10, 2020

Related U.S. Application Data

(60) Provisional application No. 62/556,743, filed on Sep. 11, 2017.

(51) Int. Cl.
*A61M 25/00* (2006.01)
*A61L 29/08* (2006.01)
*B65B 55/16* (2006.01)

(52) U.S. Cl.
CPC ......... *A61M 25/0017* (2013.01); *A61L 29/08* (2013.01); *A61M 25/002* (2013.01); *A61M 25/0009* (2013.01); *A61M 25/0045* (2013.01); *B65B 55/16* (2013.01); *A61L 2300/216* (2013.01); *A61L 2300/30* (2013.01); *A61L 2420/08* (2013.01); *A61M 2025/0019* (2013.01)

(58) Field of Classification Search
CPC .......... A61M 25/0017; A61M 25/0009; A61M 25/002; A61M 25/0045; A61M 2025/0019; A61L 29/08; A61L 2300/30; A61L 2300/08; B65B 55/16
See application file for complete search history.

(56) References Cited

U.S. PATENT DOCUMENTS

| | | | |
|---|---|---|---|
| 4,026,296 A | 5/1977 | Stoy et al. | |
| 5,084,315 A | 1/1992 | Karimi et al. | |
| 5,441,488 A | 8/1995 | Shimura et al. | |
| 10,569,047 B2 * | 2/2020 | Farrell | A61L 29/043 |
| 2001/0027299 A1 * | 10/2001 | Yang | C08L 83/04 |
| | | | 604/265 |
| 2001/0054562 A1 | 12/2001 | Pettersson et al. | |
| 2003/0023190 A1 | 1/2003 | Cox | |
| 2003/0153983 A1 | 8/2003 | Miller et al. | |
| 2005/0069272 A1 | 3/2005 | Fabian et al. | |
| 2006/0058777 A1 * | 3/2006 | Nielsen | A61L 29/16 |
| | | | 604/329 |
| 2007/0287800 A1 | 12/2007 | Acquarulo et al. | |
| 2011/0094519 A1 | 4/2011 | Gopal et al. | |
| 2012/0121919 A1 | 5/2012 | Nielsen | |
| 2013/0131647 A1 | 5/2013 | Nielsen | |
| 2013/0138088 A1 | 5/2013 | Nielsen | |
| 2014/0276915 A1 * | 9/2014 | Stout | A61L 31/08 |
| | | | 606/119 |
| 2015/0073544 A1 | 3/2015 | Gorman, III et al. | |
| 2016/0287757 A1 | 10/2016 | Belt et al. | |

FOREIGN PATENT DOCUMENTS

| | | | | |
|---|---|---|---|---|
| WO | WO 98/08884 A1 | 3/1998 | | |
| WO | WO-2007137699 A1 * | 12/2007 | | A61L 2/081 |
| WO | WO 2016/168461 A1 | 10/2016 | | |
| WO | WO 2016/205018 A1 | 12/2016 | | |
| WO | WO-2016205018 A1 * | 12/2016 | | A61L 29/043 |
| WO | WO 2018/112196 A1 | 6/2018 | | |

OTHER PUBLICATIONS

International Search Report and Written Opinion of the International Searching Authority dated Jan. 7, 2019 for International Application No. PCT/US2018/050263.
Communication Pursuant to 94(3) dated Dec. 5, 2022 for EP Application No. 18782579.9.

* cited by examiner

*Primary Examiner* — Sean M Basquill
(74) *Attorney, Agent, or Firm* — Cook Alex Ltd.

(57) ABSTRACT

Medical devices including moisture control/barrier layers over hydrophilic materials wherein the moisture control layers allow selective ingress into and egress from the hydrophilic materials. The barrier layers may also be physical barrier layers that protect the hydrophilic materials from contaminates.

17 Claims, 2 Drawing Sheets

HYDROPHILIC MEDICAL DEVICE WITH REMOVABLE MOISTURE CONTROL/BARRIER LAYER

The present application is a National Stage of PCT International Application No. PCT/US2018/050263, filed Sep. 10, 2018 which claims the benefit and priority of U.S. Provisional Patent Application No. 62/556,743, filed Sep. 11, 2017, the disclosures of all of which are hereby incorporated herein by reference.

DESCRIPTION

Technical Field

The present disclosure generally relates to hydrophilic medical devices, such as hydrophilic urinary catheters, that include a moisture control layer covering the surface of a hydrophilic material of the medical device, wherein the moisture control layer provides selective ingress and egress of water and wherein the moisture control layer is removable upon insertion of the catheter into the urethra. The present disclosure also relates to packaged medical device assemblies that include hydrophilic medical devices having a moisture control layer and methods of making the same. The present disclosure also generally relates to methods for radiation sterilization of hydrophilic coatings.

Background

It is known to coat medical devices, such as urinary catheters, with a hydrophilic coating. When the hydrophilic coating is wetted or hydrated with a wetting fluid, such as water, it becomes extremely lubricous which eases introduction of the device into the body and aids in reducing pain and discomfort associated with such introduction.

In some applications, the hydrophilically coated medical device is provided in a "dry" state wherein the user is required to wet the hydrophilic coating with a wetting fluid immediately prior to insertion into the body. In other applications, it is desirable to provide a hydrophilically coated medical device that is in a ready-to-use condition right out of the package. In the field of urinary catheters, a hydrophilically coated catheter may be provided in a catheter package wherein the catheter is stored in the package in contact with water so that the hydrophilic coating is wetted within the package and the catheter is ready for use right out of the package.

For various reasons, including but not limited to efficiency, effectiveness and cost, it is desirable to radiation sterilize packaged medical device assemblies. In some instances, the hydrophilically coated medical device and water are placed in the package and the package is sealed. After the package is sealed, the package having the hydrophilically coated medical device and water therein is exposed to radiation, such as gamma or E-Beam radiation, to sterilize the medical device. It has been found, however, that sterilization of hydrophilic coatings in the hydrated state or while in contact with a wetting fluid can result in degradation of the coating or excessive crosslinking of the coating which can lead to an increase of coefficient of friction (decrease in lubricity) of the coating and/or cause instability of coating which may result in the coating undesirably detaching from the medical device prior to or during use.

Furthermore, when the catheter is removed from a package for use, the water within the hydrophilic coating evaporates from the coating over time. This is sometimes referred to as dry-out time. If the hydrophilic coating of the catheter dries out prior to insertion into the urethra, the catheter may become less lubricious and the user may experience discomfort during use. Thus, a longer/extended dry-out time (longer time before the hydrophilic coating dries out) is generally more desirable.

Therefore, there remains a need for sterilized ready-to-use hydrophilic medical devices and methods of sterilizing hydrophilic medical devices. There also remains a need for catheters with extended dry-out times.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a medical device includes a hydrophilic material having a surface, and a moisture control layer covering at least a portion of the hydrophilic material.

In another aspect, a method of forming a urinary catheter assembly includes depositing a moisture control layer on a surface of a hydrophilic material of a urinary catheter, placing the urinary catheter in a package, and sealing the package.

In yet another aspect, a urinary catheter assembly includes a package defining a cavity and a urinary catheter located within the cavity. The urinary catheter includes a surface of a hydrophilic material, and a barrier layer covering at least a portion of the hydrophilic material.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure generally relates to hydrophilic medical devices that include a moisture control layer on a surface of the hydrophilic material of the medical device. The moisture control layers allow selective ingress of activation fluids, such as water or saline, into hydrophilic material. The moisture control layers may also allow selective egress of such fluids out of the hydrophilic material, and/or may allow both selective ingress into and egress from the hydrophilic material. The activating fluids may be a liquid and/or a vapor that hydrates the hydrophilic material. For example, the activating fluid may be liquid water and/or vapor water. Furthermore, the medical devices may be, for example, urinary catheters, endoscopes, vascular catheters and other medical devices that are inserted into the body or a lumen.

In one embodiment, the moisture control layer is a removable barrier layer that is removed from the medical device to expose the hydrophilic material of the device prior to or during use. For example, a urinary catheter may include a lubricious hydrophilic coating and a moisture control layer over the lubricious hydrophilic coating. When the urinary catheter is inserted into the urethral opening of a user, the moisture control layer may be removed from the urinary catheter. As explained in more detail below, the removal may be caused by exposing the moisture control layer to the temperature of the body which melts the moisture control layer, and/or by physical contact with tissue wherein such contact rubs or wipes the control layer from the hydrophilic coating.

Figure 1:
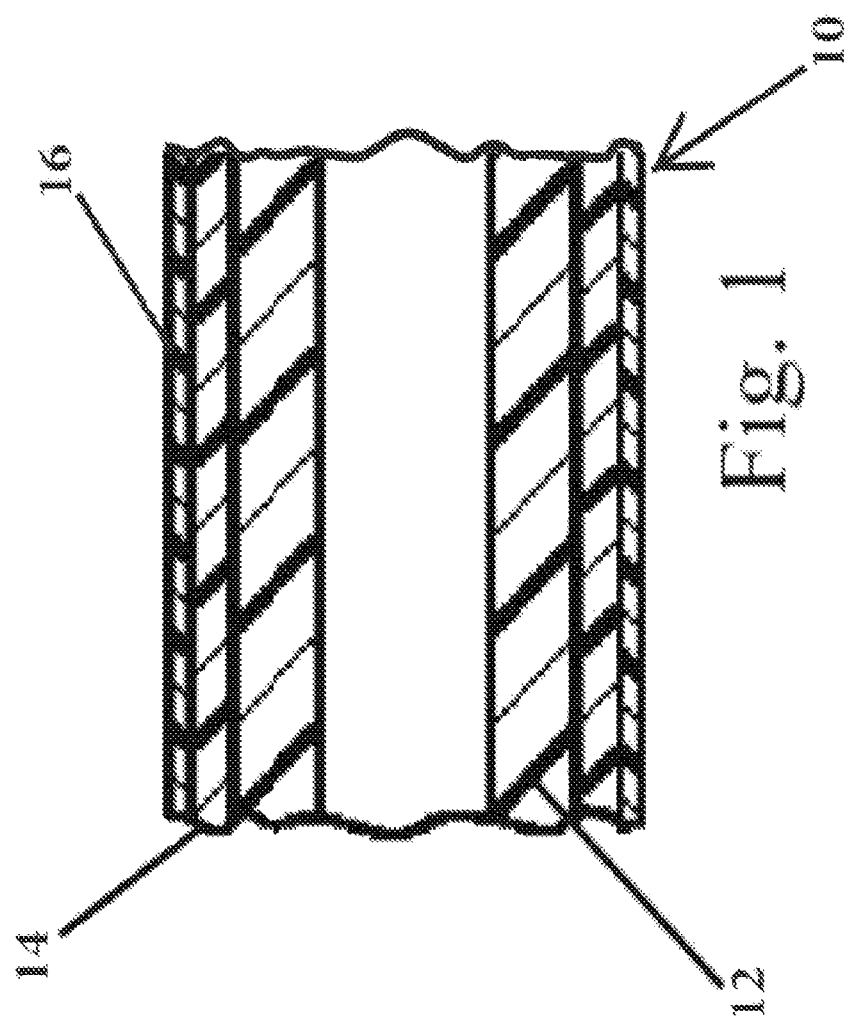
FIG. 1 is an enlarged longitudinal cross-sectional view of a portion of a hydrophilic urinary catheter which includes a moisture control layer.

FIG. 1 illustrates a portion of a hydrophilic catheter 10 in accordance with the present disclosure. The catheter 10 has a catheter shaft 12 that includes a hydrophilic material, such as hydrophilic coating 14. In other embodiments, the catheter shaft may be of a unitary structure wherein the catheter shaft itself is a hydrophilic material. A moisture control layer 16 overlies/covers/is deposited on hydrophilic coating 14. The moisture control layer allows selective ingress of activation fluid into the hydrophilic material, selective egress of activation fluid out of the hydrophilic material or both ingress and egress.

The moisture control layer may include a wax-like material or wax, such as an amphiphilic wax. In one embodiment, the moisture control layer includes a composition that includes a hydrophobic region and a hydrophilic region wherein, the hydrophilic region is attracted to and faces the hydrophilic material of the medical device and the hydrophobic region points or aligns away from the hydrophilic material of the medical device. For example, the moisture control layer may be one or more aliphatic alcohols, such as hexadecanol. Aliphatic alcohols include two distinct regions—an aliphatic region which is hydrophobic, and a region that includes an alcohol group which is hydrophilic. When a layer of aliphatic alcohol is deposited/formed on the surface of the hydrophilic material, the alcohol regions of the molecules are attracted to and align along the surface of the hydrophilic material and the aliphatic tails of the molecules point or align away from the surface of the hydrophilic material.

The moisture control layer is preferably biocompatible. Also, the moisture control layer may be configured to allow exposure of the layer or surface underlying the moisture control layer during use of the device. For example, the moisture control layer may liquefy or melt just prior to and/or during use so as to expose the layer/surface under the moisture control layer and/or the functionalities of the layer/surface (lubricity, etc.). For instance, when the medical device is a hydrophilic catheter and the moisture control layer is disposed over the lubricous hydrophilic material/surface of the catheter, during use the moisture control layer may be configured to liquefy or melt to allow exposure of the lubricious hydrophilic surface.

In one embodiment, the moisture control layer may have a melting point that has been tuned or adjusted to the desired application. For example, for medical devices that are inserted into the body, the melting point of the moisture control layer may be at or about 37° C. (at or about body temperature). In one embodiment, the moisture control layer may optionally include additives that can tune the moisture control layer to a desired melting point. For instance, the moisture control layer may include a blend of 1-hexadencanol and polyethylene distearate (PEG-distearate). The ratio of PEG-distearate to 1-hexadencanol may be sufficient to result in a moisture control layer having a desired melting point, such as a melting point of 37° C. Thus, when the device is inserted into the body, the moisture control layer melts, thereby exposing the underlying surface. In other embodiments, the thickness and melting point of the moisture control layer may be varied to allow exposure of the underlying surface. For example, the moisture control layer may be substantially composed of 1-hexadecanol, which has a melting point of about 49° C. The thickness of the moisture control layer may be such that the moisture control layer does not necessarily completely melt to expose the underlying surface. In other words, the moisture control layer may be a thin layer that when warmed exposes the underlying surface or the functionality of the underlying surface (e.g., the lubricious functionality of a hydrophilic surface).

Alternatively or in addition to melting, the moisture control layer may also be rubbed or wiped off prior to or during use. For example, when a urinary catheter is inserted into the urethral opening, contact between the tissue at or near the urethral opening and the moisture control layer may rub or wipe off the moisture control layer from the catheter so as to remove the layer and expose the lubricious hydrophilic material. In one embodiment, the urinary catheter may include an introducer tip which is inserted into the urethra opening prior to inserting the catheter. After the introducer tip has been inserted into the urethral opening, the catheter is inserted into the urethra through the introducer tip. As the catheter is inserted through the introducer tip, contact between the moisture control layer and the introducer tip may remove the moisture control layer and expose the hydrophilic layer. In yet another embodiment, the catheter may include a gripping aid that slides along the catheter and allows the user to grip the catheter through the gripping aid. As the gripping aid contacts the catheter during use, such contact may rub or wipe off the moisture control layer.

In one embodiment of forming the moisture control layer on the surface of the hydrophilic material, an aliphatic alcohol(s) is dissolved in ethanol, optionally with a spreading agent or other additive, such as polyethylene glycol or PEG-distearate. The solution is then deposited on the surface of the hydrophilic material and the ethanol is dried off, thereby forming a moisture control layer/coating on the surface of the hydrophilic material. For example, a solution including about 1% hexadecanol in ethanol and, optionally, a spreading agent or other additive, may be deposited on the hydrophilic surface of a urinary catheter. The solution may be applied by dip coating, brushing, spraying (such as by aerosol spraying) or any other suitable application method. The ethanol is then dried off to form a moisture control layer over the surface of the hydrophilic material of the catheter. The coating may be formed on at least a portion of the surface or may substantially cover the entire surface of the hydrophilic material. Furthermore, preferably the moisture control layer is a thin film or molecular monolayer (e.g. a layer that is one molecule thick). For example, the moisture control layer may be a molecular sleeve that is a monolayer or is a couple of molecular layers thick. In one embodiment, the moisture control layer may have a thickness of about between about 2 nm and 10 nm. In other embodiments, the thickness may be greater or smaller depending on the desired application.

Figure 2:
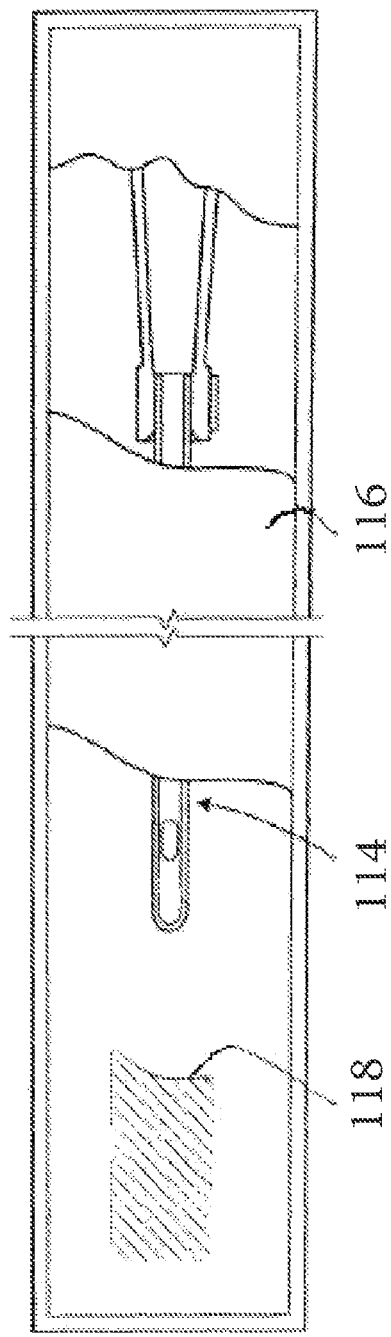
FIG. 2 is a top plan view of a urinary catheter shown within a package.

In one method of forming a sterilized catheter assembly, a moisture control layer is formed on at least a portion of the surface of a hydrophilic material of a hydrophilic urinary catheter. Referring to FIG. 2, the catheter 114 is then placed in the cavity of a package 116 with an activation fluid or hydration medium 118, such as water, and the package is sealed. In one embodiment, the activation fluid may be liquid water in direct contact with the catheter. In another embodiment, the activation fluid may be a vapor. For example, the catheter and liquid water may be within separate compartments of the cavity of the package wherein the compartments are separated by a liquid impermeable, vapor permeable barrier. The liquid water may donate a vapor that activates the hydrophilic material of the catheter. Whether the activation fluid is a liquid or a vapor, the moisture control layer delays hydration of the hydrophilic material by the activation fluid. That is the moisture control layer allows selective ingress of the activation fluid into the hydrophilic material. In one embodiment, the hydrophobic region of the moisture control layer partially retards water from the hydrophilic material.

After the package has been sealed, but before the hydrophilic material of the catheter has been fully hydrated, the package is exposed to sterilizing radiation, such as gamma or E-beam radiation. In one embodiment, the hydrophilic material is substantially dry or minimally hydrated. Because the moisture control layer selectively limits the amount of hydration fluid ingress into the hydrophilic layer, the hydrophilic material is sterilized in a dry, substantially dry or a not fully hydrated state. This limits or reduces the complications associated with radiation sterilizing a hydrophilic material while it is in a substantially hydrated state.

After the package is sterilized, the distribution of the package is delayed for a period of time to allow ingress or further ingress of activation fluid through the moisture control layer and into the hydrophilic material so as to allow the hydrophilic material to become substantially or fully hydrated.

When the user opens the package for use, the moisture control layer may also then prevent the egress of the hydration fluid from the hydrophilic coating, which desirably leads to extended dry-out times. That is, the moisture control layer selectively reduces the amount of activation fluid evaporating from the hydrophilic material. When the catheter is inserted into the urethral opening, the moisture control layer may be removed in any of the above described manners, i.e. melting and/or rubbing. Removal of the moisture control layer exposes the lubricious hydrophilic coating to ease advancement through the remainder urethra.

In another embodiment of a method of forming a catheter assembly, the hydrophilic material of the catheter is hydrated and then the moisture control layer is formed on the surface of the hydrophilic catheter. The catheter is then placed into the cavity of a package and the package is sealed. When the user opens the package for use, the moisture control layer may prevent the egress of the hydration fluid from the hydrophilic coating, which desirably leads to extended dry-out times.

The thin film or molecular sleeves described above may also serve as a removable physical barrier that prevents or reduces contamination of the hydrophilic surface of urinary catheter prior to insertion into the urethra. For example the thin film or molecular sleeves may be a barrier that prevents the hydrophilic surface from being contaminated with microbes, dust or other particles. When the catheter is taken out of the package for use, it is may be exposed to contaminates in the surrounding environment. When the catheter includes a thin film or molecular sleeve barrier, the contaminants come into contact with the barrier and not the hydrophilic surface. When the barrier is removed prior to or during use (melting or rubbing off), the contaminants may remain with the material of the removed barrier (e.g. at the urethral opening) and are not transported with the catheter. That is, when the catheter is inserted into the urethral opening, the barrier is removed and the material of the barrier and any contaminants thereon remain at or near the urethral opening while the uncontaminated now exposed portion of the catheter is advanced through the urethra.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A urinary catheter assembly, comprising:
   a package defining a cavity;
   a urinary catheter located within the cavity, the urinary catheter including a surface of a hydrophilic material provided on the exterior surface of the urinary catheter; and
   a moisture control layer covering at least a portion of the hydrophilic material wherein the moisture control layer comprises a wax.

2. The urinary catheter assembly of claim 1 wherein the hydrophilic material is a hydrophilic coating.

3. The urinary catheter assembly of claim 1 herein the hydrophilic material is in a hydrated state.

4. The urinary catheter assembly of claim 1 wherein the hydrophilic material is in a substantially dry state.

5. The urinary catheter assembly of claim 1 wherein the moisture control layer provides a selective ingress of water into the hydrophilic material.

6. The urinary catheter assembly of claim 1 wherein the moisture control layer provides a selective egress of water from the hydrophilic material.

7. The urinary catheter assembly of claim 1 wherein the wax comprises an amphiphilic wax.

8. The urinary catheter assembly of claim 1 wherein the moisture control layer further comprises one or more aliphatic alcohols.

9. The urinary catheter assembly of claim 8 wherein the aliphatic alcohol comprises hexadecanol.

10. A urinary catheter assembly, comprising:
    a package defining a cavity;
    a urinary catheter located within the cavity, the urinary catheter including a surface of a hydrophilic material provided on the exterior surface of the urinary catheter; and
    a moisture control layer covering at least a portion of the hydrophilic material
    wherein the moisture control layer comprises hexadecanol.

11. The urinary catheter assembly of claim 10 wherein the hydrophilic material is a hydrophilic coating.

12. The urinary catheter assembly of claim 10 herein the hydrophilic material is in a hydrated state.

13. The urinary catheter assembly of claim 10 wherein the hydrophilic material is in a substantially dry state.

14. The urinary catheter assembly of claim 10 wherein the moisture control layer provides a selective ingress of water into the hydrophilic material.

15. The urinary catheter assembly of claim 10 wherein the moisture control layer provides a selective egress of water from the hydrophilic material.

16. The urinary catheter assembly of claim 10 wherein the moisture control layer further comprises a wax.

17. The urinary catheter assembly of claim 16 wherein the wax comprises an amphiphilic wax.

* * * * *